United States Patent [19]

Davis

[11] Patent Number: 4,725,593
[45] Date of Patent: Feb. 16, 1988

[54] METHOD OF TREATING SMOOTH MUSCLE SPASM

[75] Inventor: William M. Davis, Tucson, Ariz.

[73] Assignee: United Pharmaceuticals, Inc., Tucson, Ariz.

[21] Appl. No.: 853,378

[22] Filed: Apr. 15, 1986

Related U.S. Application Data

[63] Continuation of Ser. No. 703,262, Feb. 20, 1985, abandoned.

[51] Int. Cl.[4] .................... A61K 31/54; A61K 31/265
[52] U.S. Cl. ........................... 514/210; 514/211; 514/212; 514/218; 514/222; 514/223; 514/224; 514/236; 514/255; 514/297; 514/317; 514/320; 514/324; 514/325; 514/365; 514/374; 514/385; 514/422; 514/428; 514/513
[58] Field of Search ............... 514/210, 211, 212, 218, 514/222, 223, 224, 236, 255, 297, 317, 370, 324, 325, 365, 374, 385, 422, 478, 513

[56] References Cited

U.S. PATENT DOCUMENTS 2,390,555 12/1945 Richardson ......................... 544/158
4,432,977 2/1984 Davis .................................. 514/513
4,647,562 3/1987 Davis .................................. 514/222

FOREIGN PATENT DOCUMENTS 2003680 8/1971 Fed. Rep. of Germany .

OTHER PUBLICATIONS

Dupre. Levy and Tchoubar Compte Rendue de la Society de Biologie, 140. pp. 477–479 (1946).
Tchoubar and Letellier-Dupre. Bulletin de la Society Chimique pp. 792–794, Liberman, Farmakol i. Toksikol. pp. 10–17 (1956).
C. A. Buehler et al., J. Med. Chem., 6, pp. 230–233 (1963).
R. O. Clinton et al., J. Amer. Chem. Soc. 66, pp. 2076–2077 (1946).
Chemical Abstracts Service Registry No. 79564–01–5, pp. 2771 RJ, dated 1981, Supp.
Okuyama et al., Reaction of Thiols With Phenylglyoxal to Give Thioesters of Mandelic Acid 2 Intramolecular General-Base Catalysis and Change in Rate Determining Step, J. Amer. Chem. Socl. 104(9), pp. 2582–2587, dated 1982.
Goodman and Gilman's: The Pharmacological Basis of Therapeutics, 6th ed. Macmillan Publishing Co., New York, NY 10022, p. 132.
Chemical Abstracts Service Registry No. 527234a (Tohoku Coll. Pharm., Sendai), 1958.

Primary Examiner—Richard L. Raymond
Attorney, Agent, or Firm—Austin R. Miller

[57] ABSTRACT

A new method of treating a patient suffering smooth muscle spasm comprises administering to the patient an effective amount of anti-spasmodic compound having the general formula:

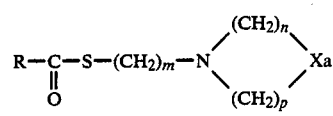

where R is selected from the group consisting of:

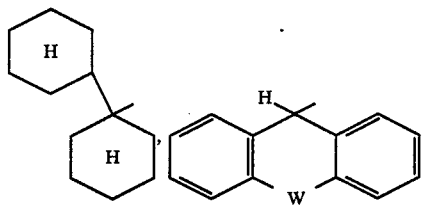

wherein W is $CH_2$, NH, O or S,

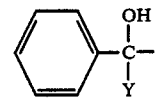

wherein Y is an alicyclic ring ring having 3–12 carbon atoms, and

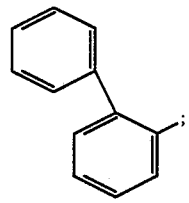

the total number of carbon atoms in R is equal to or less than 20. Furthermore, m is an integer from 1 to 4, n is an integer from 1 to 4, p is an integer from 1 to 4 and q is an integer from 1 to 4. X may be nonexistent or may be 0, S, NH or $CH_2$ or salts thereof. However, when X is nonexistent the terminal group in both the n-chain and the p-chain is a methyl group provided that a is zero or 1 and when a is 1, X is selected from the group consisting of 0, S, and $CH_2$ and n and p are integers from 1 to 4; and when a is 0 then X is nonexistent and n and p are integers from 1 to 4 and the terminal group in both the n-chain and the p-chain is methyl; and pharmaceutically acceptable salts thereof.

6 Claims, No Drawings

METHOD OF TREATING SMOOTH MUSCLE SPASM

This application is a continuation of application Ser. No. 703,262 filed 2/20/85, now abandoned.

BACKGROUND OF THE INVENTION

1. Field of the Invention

The present invention relates to new methods of treating a patient suffering from smooth muscle spasm and particularly to new metods of administering pharmaceutical compounds having useful anti-spasmodic properties.

2. Description of the Prior Art

The purpose of an anti-spasmodic drug is to relieve spasms of the smooth muscles. Smooth muscles line most of the visceral organs. The peristalsis and muscular activity of the stomach, intestines, gall bladder, urinary bladder, lung, the uterus, and to a degree the heart are all largely controlled by smooth muscles. Smooth muscles are innervated by the autonomic nervous system. The autonomic nervous system consists of two antagonistic branches—the sympathetic branch and the parasympathetic branch. On all visceral organs except the heart the parasympathetic nerve impulses increase the irritability and tension of the smooth muscles; contrariwise, the sympathetic nerve impulses increase the tension and irritability of the muscles of the heart muscle and relax the smooth muscles of the other visceral organs.

A spasm in a smooth muscle may be due to one of two causes. Either the smooth muscle may be receiving exaggerated impulses from the autonomic nervous system which create violent contractions in the muscle, or the muscle may be intrinsically stimulated into a spasm (most likely from chemical changes in the surrounding tissue). A spasm due to exaggerated impulses from the parasympathetic branch of the autonomic nervous system may often be corrected by administering atropine (an active alkaloid of belladonna which serves to break a connection between the parasympathetic nerve and the smooth muscle. This ability and effect of atropine is called a "neurotropic effect". A spasm intrinsic in the smooth muscle itself may often be corrected by papaverine (a derivative of opium which is classed as a narcotic). Papaverine has an ability to decrease intrinsically the contractility of smooth muscle; it has the ability to relax smooth muscles directly. This ability and effect of papaverine is called a "musculotropic effect."

In relieving spasms of smooth muscles generally, a musculotropic effect is acknowledged to be superior to a neurotropic effect. A neurotropic effect cannot relieve spasms intrinsic in the smooth muscle itself, while a musculotropic effect, by relaxing and decreasing the irritability and responsiveness of smooth muscle to stimulation from the autonomic nervous system, can help to relieve a smooth muscle spasm even when it is due to exaggerated impulses from the autonomic nervous system.

A clinical difficulty with atropine is that of undesirable side-reactions. Atropine when given in effective doses, serves to break or partly break all the parasympathetic nerve-smooth muscle connections throughout the body. Thus when atropine is given in sufficient dosage to relieve a spasm in a specific visceral organ, such as a gastric or intestinal spasm (the spasm caused by exaggerated nerve impulses from the parasympathetic nervous system) undesirable side-actions due to the breaking of the parasympathetic nerve-muscle connections elsewhere in the body may occur. The most easily recognized of these undesirable side reactions are dilation of the pupil and dryness of the mouth, caused by the breaking of the parasympathetic connections to the iris and the saliva producing mechanism respectively.

Atropine is acknowledged to have also a musculotropic effect, but its neurotropic effect is so strong that it cannot be given in greater than minute doses (1/60 to 1/40 grain) without encountering the undesirable side reactions. This dosage is too small to permit a significant musculotropic effect.

U.S. Pat. No. 2,390,555 discloses a class of compounds comprising di-N-substituted aminoethyl esters of diphenylthioacetic acid of the general formula $(C_6H_5)_2$—CH—COS—$CH_2CH_2$—R in which R represents a disubstituted amino radical of either the diethylamino group, the morpholino group or the piperidino group. This patent was based upon the discovery that the thio analogs of certain disubstituted acetic acid esters of aminoalcohols have desirable anti-spasmodic properties. These compounds have proven to be very effective and are widely used as anti-spasmodics without encountering the undesirable side reactions due to excessive neurotropic effect.

U.S. Pat. No. 4,432,977 discloses new uses, especially for the dilation of the smooth muscles of the upper urinary tract, of the compounds disclosed in U.S. Pat. No. 2,390,555.

In *Compte Rendu de la Societe de Biologie*, 140, pp 477–9, (1946) Dupre, Levy and Tchoubar disclose a series of compounds having the formula $C_6H_5(R)CH$—C(O)—S—$CH_2CH_2N(CH_2CH_3)_2$ where R is either a phenyl group, a propyl group, an isopropyl group, a butyl group or an isoamyl group. These compounds are all disclosed as being spasmolitic agents.

Compounds of the same general formula given above were prepared by Tchoubar and Letellier-Dupre in *Bulletin de la Societe Chimique*, pp 792–4 (1947) wherein R was a phenyl group, an ethyl group, a propyl group, an isopropyl group, a butyl group, an isoamyl group or hydrogen.

In *Farmakol. i. Toksikol.*, pp 10–17 (1956), Liberman discloses a class of compounds having the general formula $(C_6H_5)_2CHCOSCH_2CH_2N$—$R_2$, wherein both R's are the same and are selected from methyl, ethyl, propyl and butyl groups; and a class of compounds having the general formula $(C_6H_5)$—$CH(C_6H_{11})COSCH_2CH_2N$—$R_2$, wherein both R's are the same and are selected from methyl, ethyl, propyl and butyl groups.

C. A. Buehler et al in the *Journal of Medicinal Chemistry*, 6, pp 230-3 (1963) disclose physiologically active compounds of the general formula R(R')—C(OH)-COS$(CH_2)_2NR''_2$ wherein R and R' are aryl groups.

R. O. Clinton et al in the *Journal of the American Chemical Society*, 68, pp 2076–7 (1946) synthesized a number of dialkyl aminoalkyl diarylthiolacetates including fluorene-9-carbothioic acid, S-[2-diethylaminoethyl] ester.

SUMMARY OF THE INVENTION

A new method of treating a patient suffering smooth muscle spasm comprises administering to the patient an effective amount of an anti-spasmodic compound having the general formula:

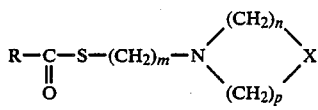

where R is selected from the group consisting of:

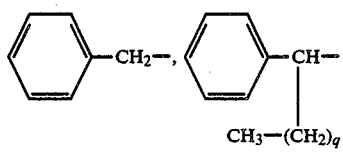

wherein q is an integer from 2 to 4,

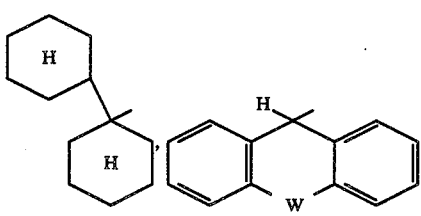

wherein W is CH₂, NH, O or S,

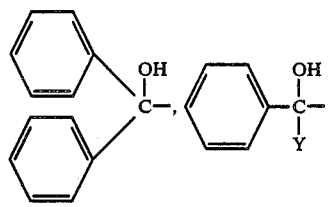

wherein Y is an alicyclic ring having 3–12 carbon atoms, and

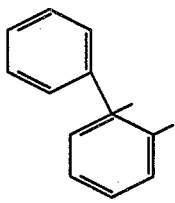

The total number of carbon atoms in R is equal to or less than 20. Furthermore, m is an integer from 1 to 4;
n is an integer from 1 to 4;
p is an integer from 1 to 4; and
X may be nonexistent or may be O, S, NH or CH₂ or salts thereof, but when X is nonexistent the terminal group in both the n-chain and the p-chain is a methyl group.

A preferred sub-genus of the compounds having the above described general formula comprises the following:

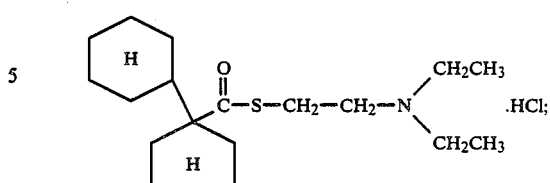

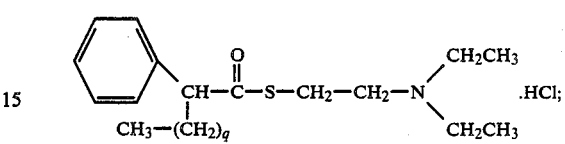

wherein q = 2–4.

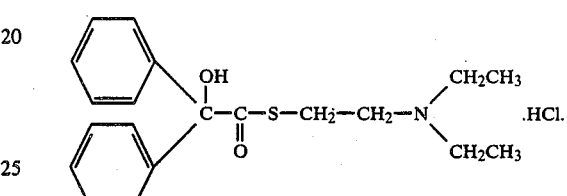

The present invention comprises methods of administering the above-described compounds for, but not limited to, the treatment of patients suffering from pylorospasm in the upper and lower gastrointestinal tract, spasm associated with the gall bladder and common bile duct, as well as diarrhea, the irritable bowel syndrome, ureterospasm, bladder irritation, asthma and emphysema.

DESCRIPTION OF THE PREFERRED EMBODIMENTS

The anti-spasmodic compounds used in the methods of the present invention are effective in a dosage range of from about 1 to about 15 mg/kilogram of body weight per day. A preferred dosage is in the range of from about 1.5 to about 11.5 mg/kilogram of body weight per day. A still more preferred dosage range is from about 3 to about 6 mg/kilogram of body weight per day.

The anti-spasmodic compounds used in the methods of the present invention may be combined with a pharmaceutically acceptable carrier and can be administered orally, typically in tablets of 400 mg active ingredient, total 1155 mg, or by intravenous injection, or by topical application.

Because the anti-spasmodic compounds used in the methods of the present invention generally hydrolyze slowly in water, they are preferably not used as a serum or suspension unless used as a freshly prepared solution. It is possible, however, to encapsulate microspheres of these compounds in the form of a liquid suspension for administration to patients.

As specific examples of the compounds used in the methods of the present invention, there can be mentioned:

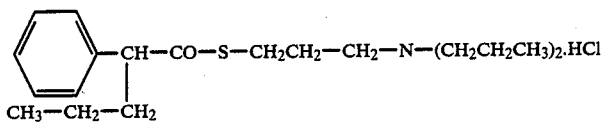
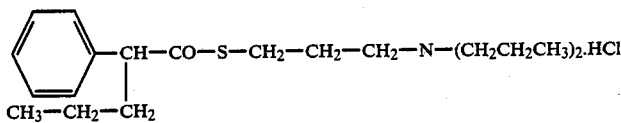
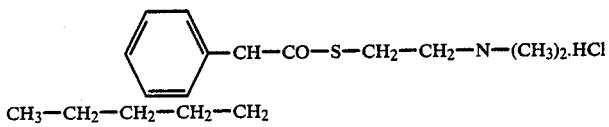
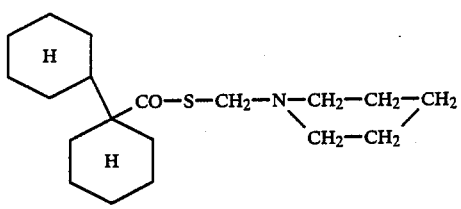
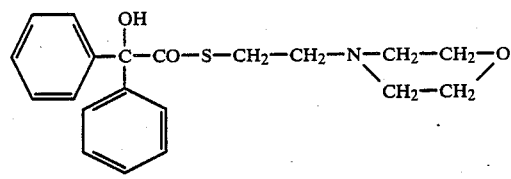
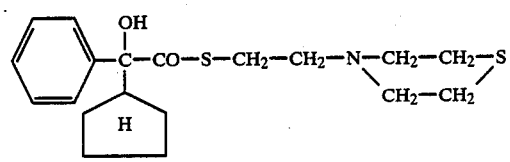
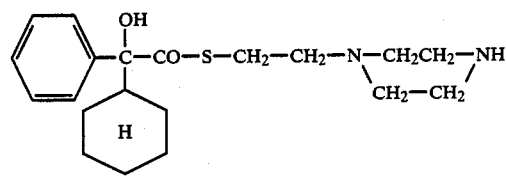
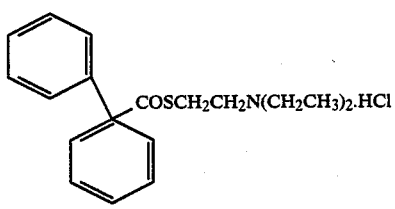
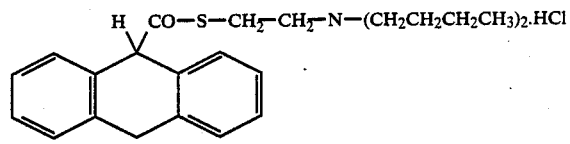
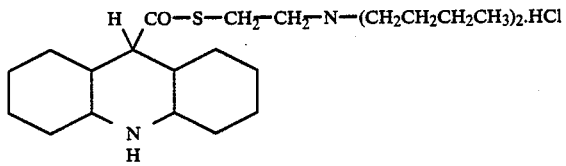
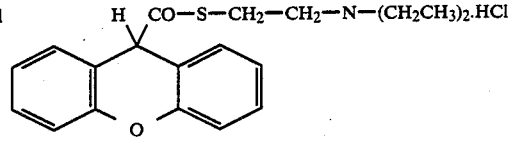
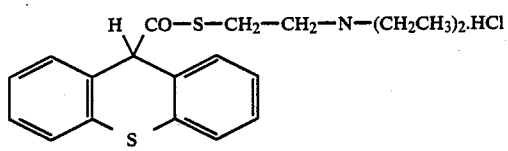
The general reaction used in the synthesis of the anti-spasmodic compounds described in the following examples of the present invention involves the nucleophilic substitution of certain acyl chlorides with certain thiol compounds, such as 2-diethylaminoethanethiol. This reaction is illustrated in the following formula, wherein R is as defined above:
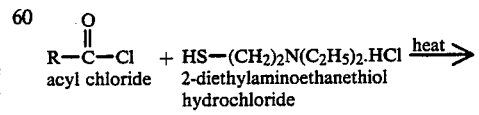
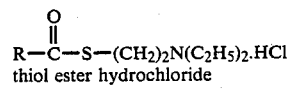

2-diethylaminoethanethiol was purified by re-distillation in vaccuo and nitrogen gas. Subsequently, the thiol was reacted with various acyl chlorides in dichloromethane by combining the two reactants in a 1:1 molar ratio and gently heating under reflux condensation for approximately 1–2 hours. The reaction mixture was then cooled in ice-water until crystallization occurred or, if necessary, in dry ice-ethanol. The crude crystals were harvested by suction filtration and were then recrystallized from an appropriate solvent (e.g. ethyl acetate, acetone, petroleum ether, or dichloromethane).

The desired acyl chlorides may be prepared from the carboxylic acid analogues by reaction with oxalyl chloride as follows:

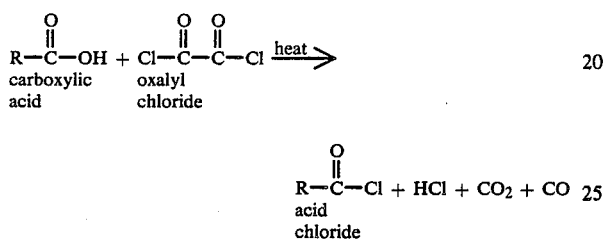

The reaction was performed under reflux condensation. Following the reaction, which was usually complete within a few hours, the acid chlorides were vacuum-distilled and reacted with a thiol compound as described above.

The compounds of this invention are anti-muscarinic agents (cholinergic-muscarinic receptor antagonists) which inhibit the actions of acetylcholine on autonomic effectors innervated by postganglionic cholinergic nerves as well as on smooth muscle that lacks cholinergic innervation. Since a major component of parasympathetic control of smooth muscle occurs via muscarinic receptors, these compounds are effective as modifiers of smooth muscle activity.

Thiphenamil hydrochloride has been shown to decrease spasm of the gastrointestinal tract, biliary tract, ureter and uterus without producing characteristic atropinic side effects on salivary and sweat glands, GI glands, the eye or the cardiovascular system. This invention results in compounds which are as efficacious as thiphenamil hydrochloride, or more so, in relaxing various smooth muscle systems while at the same time demonstrating thiphenamil hydrochloride's lack of associated side-effects.

The following is claimed:

1. A method of treating a patient suffering smooth muscle spasm comprising administering to the patient an effective amount of a compound having the formula:

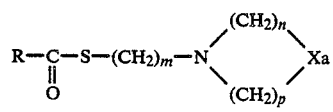

wherein R is selected from the group consisting of:

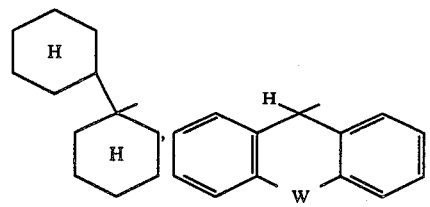

wherein W is $CH_2$, NH, O or S,

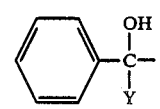

wherein Y is an alicyclic ring ring having 3–12 carbon atoms, and

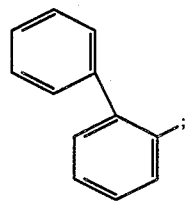

the total number of carbon atoms in R is equal to or less than 20, and wherein
  a is zero or 1
  m is an integer from 1 to 4;
  n is an integer from 1 to 4;
  p is an integer from 1 to 4; and
  provided that when a is 1, X is selected from the group consisting of O, S, NH and $CH_2$ and n and p are integers from 1 to 4; and when a is O then X is nonexistent and n and p are integers from 1 to 4 and the terminal group in both the n-chain and the p-chain is a methyl; and pharmaceutically acceptable salts thereof.

2. A method of treating a patient suffering smooth muscle spasm comprising administering to the patient an effective amount of a compound having the formula:

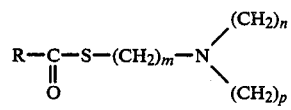

wherein R is

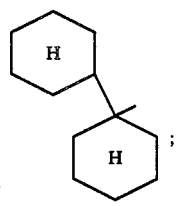

the total number of carbon atoms in R is equal to or less than 12, and wherein
  m is an integer from 1 to 4;

n is an integer from 1 to 4;

p is an integer from 1 to 4; and the terminal group in both the n-chain and the p-chain is a methyl group; and pharmaceutically acceptable salts thereof.

3. The method as defined in claim 1 or 2, wherein the compound is administered in a dosage of from about 1 to about 15 mg/kg of body weight per day.

4. The method as defined in claim 1 or 2, wherein the compound is administered in a dosage of from about 1.5 to about 11.5 mg/kg of body weight per day.

5. The method as defined in claim 1 or 2, wherein the compound is administered in a dosage of from about 3 to about 6 mg/kg of body weight per day.

6. The method as defined in claim 1 or 2, wherein the compound is combined with a pharmaceutically acceptable carrier.

* * * * *

UNITED STATES PATENT AND TRADEMARK OFFICE
CERTIFICATE OF CORRECTION

PATENT NO. :   4,725,593

DATED       :   February 16, 1988

INVENTOR(S) :   William M. Davis

It is certified that error appears in the above-identified patent and that said Letters Patent is hereby corrected as shown below:

Column 3, fifth drawing, remove extended lines.

Old Drawing 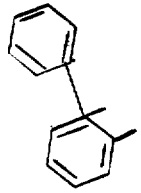

New Drawing 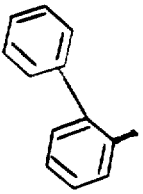

Column 5, first drawing, add a 2 to the first row of symbols on first line and delete the second set of symbols on bottom of figure.

Old Drawing

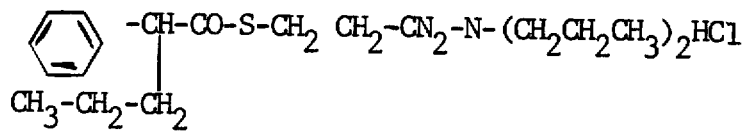

New Drawing

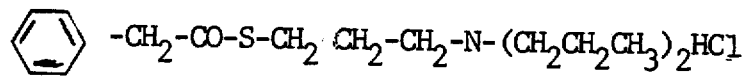

UNITED STATES PATENT AND TRADEMARK OFFICE
CERTIFICATE OF CORRECTION

PATENT NO. : 4,725,593
DATED : February 16, 1989
INVENTOR(S) : William M. Davis

It is certified that error appears in the above-identified patent and that said Letters Patent is hereby corrected as shown below:

Column 5, third drawing, add line connecting first symbol on first line to last symbol on bottom line.

New Drawing

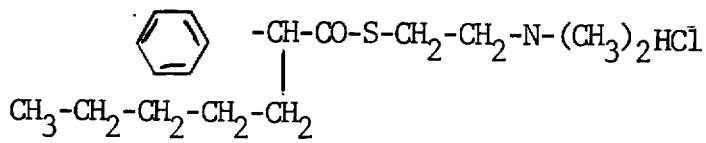

Old Drawing

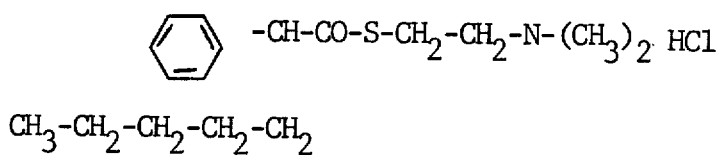

Signed and Sealed this

Twenty-third Day of January, 1990

Attest:

JEFFREY M. SAMUELS

Attesting Officer     Acting Commissioner of Patents and Trademarks